United States Patent
Ling et al.

[11] Patent Number: 6,123,730
[45] Date of Patent: Sep. 26, 2000

[54] PROSTHESIS CONSTRUCTION

[75] Inventors: Robin Sydney Mackwood Ling, Dartmouth; Graham Allan Gie, Yeoford; Andrew John Timperley, Exeter, all of United Kingdom; John Andrew Storer, Bayeux, France

[73] Assignee: Benoist Girard SAS, France

[21] Appl. No.: 09/323,616

[22] Filed: Jun. 1, 1999

[30] Foreign Application Priority Data

Jun. 4, 1998 [GB] United Kingdom .................... 9812066

[51] Int. Cl.[7] ........................................................ A61F 2/36

[52] U.S. Cl. ...................................... 623/23.25; 623/23.48

[58] Field of Search ................................... 63/23.25, 23.48

[56] References Cited

U.S. PATENT DOCUMENTS

| | | | |
|---|---|---|---|
| 5,116,380 | 5/1992 | Hewka et al. | 623/23 |
| 5,163,963 | 11/1992 | Hewka et al. | 623/23 |
| 5,290,311 | 3/1994 | Baumann | 623/23 |
| 5,314,489 | 5/1994 | Hoffman et al. | 623/22 |
| 5,340,362 | 8/1994 | Carbone | 623/23 |
| 5,549,705 | 8/1996 | Michielli et al. | 623/23 |
| 5,755,793 | 5/1998 | Smith et al. | 623/16 |

*Primary Examiner*—David J. Isabella
*Attorney, Agent, or Firm*—Lerner, David, Littenberg, Krumholz & Mentlik, LLP

[57] ABSTRACT

A prosthesis provided with a stem for fixation with cement in a bone socket, the proximal portion of the stem being provided with a number of shaped projections which are dimensioned to contact the inner wall of the bone socket and to act to guide the proximal end of the stem therein.

21 Claims, 1 Drawing Sheet

PROSTHESIS CONSTRUCTION

BACKGROUND OF THE INVENTION

1. Field of the Invention

This invention relates to a prosthesis construction wherein the stem of the prosthesis is provided with means to centralise its proximal end in a bone socket.

2. Description of Prior Art

According to the present invention in a prosthesis provided with a stem for fixation with cement in a bone socket, the proximal portion of the stem is provided with a number of shaped projections which are dimensioned to contact the inner wall of the bone socket and to act to guide the proximal end of the stem therein. Such a stem as shown in U.S. Pat. Nos. 5,116,380 and 5,163,963.

In a preferred construction said projections are fastened to said stem by detachable attachment means which can release if there is subsequent downward movement of the stem in the bone socket after initial implantation.

Said projections may be of teardrop shape facing towards the proximal or distal ends of the stem.

The attachment means can be provided by a releasable adhesive, shear pins or by relying upon the relative adhesion between a smooth surface on the projection and a smooth surface on the stem.

The projections can be made of any convenient material, for example polymethylmethacrylate (PMMA).

In one preferred construction the projections are located on the corners of a stem which is of triangular, square or rectangular cross-section.

BRIEF DESCRIPTION OF THE DRAWINGS

The invention can be performed in various ways and some embodiments will now be described by way of example and with reference to the accompanying drawings in which.

DESCRIPTION OF THE PREFERRED EMBODIMENTS

Figure 1:
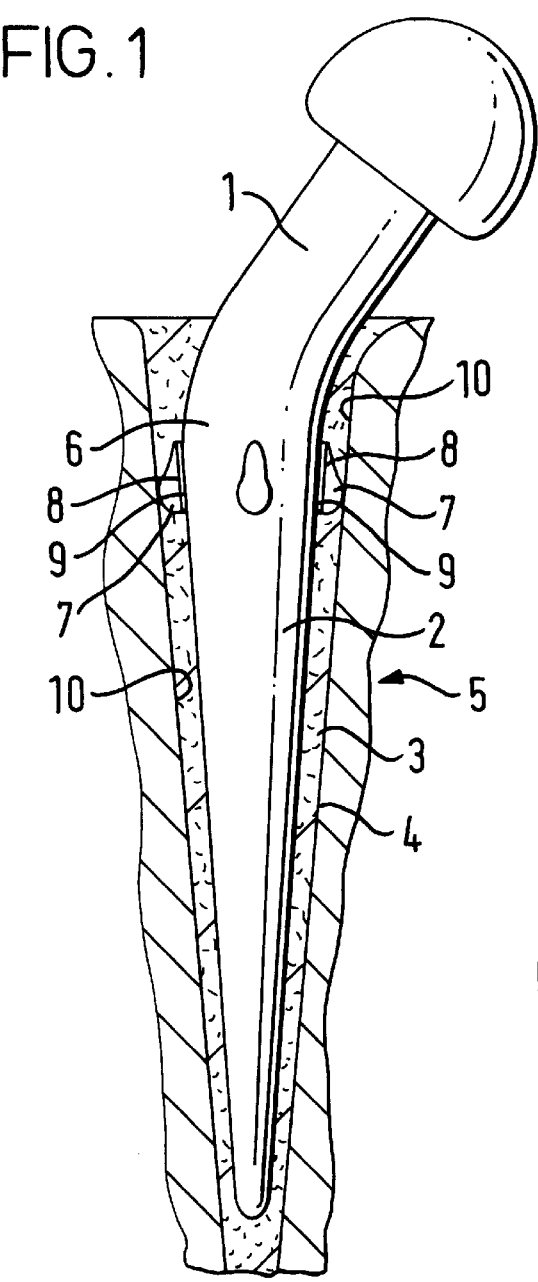
FIG. 1 is a side elevation of a femoral prosthesis embodying the invention in place in a bone socket.

As shown in FIG. 1 a femoral prosthesis 1 is provided with the invention. The prosthesis 1 includes a stem 2 for fixation with cement 3 in a bone socket 4 provided in the patient's femur 5. A proximal portion 6 of the stem 2 is provided with a number (four) of shaped projections 7 which are arranged in a ring around the prosthesis stem. The general cross-section of the stem, as shown in FIG. 1, is rectangular and a projection 7 is provided on each face.

Each of the projections 7 is of a teardrop shape with a flat back 8. The projections 7 are fastened to the stem 2 by detachable attachment means which, in this construction, are provided by a thin layer of releasable adhesive 9.

The projections are dimensioned so that their outer faces contact the inner wall 10 of the bone socket 4 and act to guide the proximal end 6 of the stem 2 therein.

The releasable cement is sufficiently adhesive to retain the projections in place when the prosthesis is inserted and until they engage the inner wall 4 of the socket. The prosthesis shown is of the shoulderless type and if there is subsequent downward movement of the stem 7 in the bone socket after initial implantation the adhesive will release to accommodate this further movement.

The projections can be made from any convenient material, for example metal or a synthetic plastics material, and they can be made from polymethylmethacrylate (PMMA) if desired.

The stems of prostheses which are intended to have subsequent downward movement are usually highly polished and in this case it is possible to provide the rear wall 8 of each projection with a similar smooth surface so that the projections can be placed in position and will retain their position due to the relative adhesion between the two smooth surfaces. If however there is subsequent downward movement of the stem the adhesion between the surfaces will release.

Figure 2:
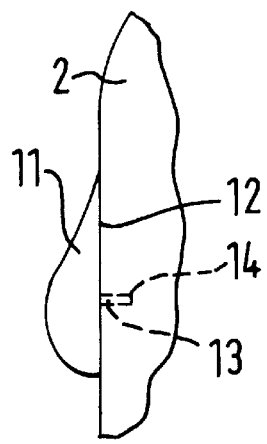
FIG. 2 is a side elevation of an alternative form of projection.

FIG. 2 shows an alternative projection construction in which each projection is again of a teardrop shape with a flat back 12. Each projection is provided with a small shear pin 13 which engages in a socket 14 in the wall of the stem 2. The shear pin 13 is sufficient to hold the projection in place but is weak enough to shear if there is subsequent downward movement of the stem in the cemented socket.

If the projection is made from a synthetic plastics material the shear pin 13 can be integral with it.

In an alternative embodiment (not shown) the shear pin 13 could be a separate member located in the socket 14 but protruding from it and the projection 11 could have a similar socket to accept it.

Figure 3:
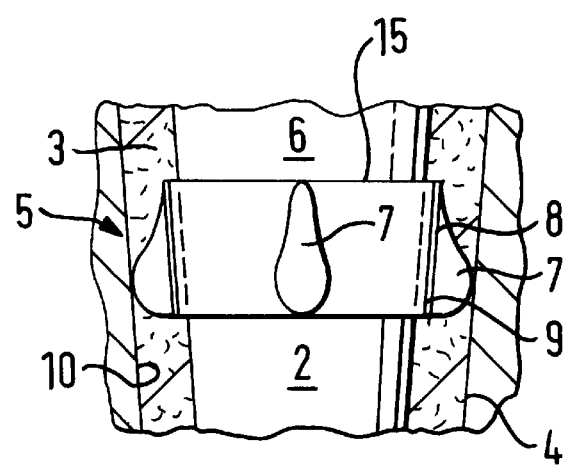
FIG. 3 is a side elevation of another construction according to the invention; and, FIG. 4 is a cross-sectional end elevation of a stem of rectangular cross-section incorporating the invention.

In an alternative construction shown in FIG. 3 the same numerals are used to indicate similar parts to those used in FIG. 1 but in this arrangement the shaped projections are carried on a band or collar 15 which is shaped and dimensioned to be located on the proximal portion 6 of the stem 2. The band is retained in position due to the taper on the stem 2 and the projection 7 can again be held in place by an adhesive or by the shear pin arrangement shown in FIG. 2. The band can be made of any convenient material, for example metal or a synthetic plastics material.

As shown in the above constructions the teardrop shape of the projections is arranged so that the thinner end of the teardrop points towards the proximal end of the stem but they could alternatively be arranged so that the thinner end of the teardrop pointed towards the distal end of the stem. In certain circumstances this latter construction might assist insertion of the stem into the canal.

Figure 4:
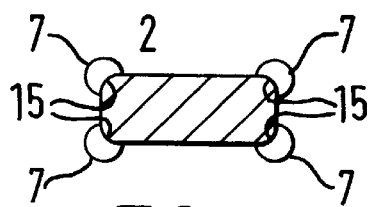

FIG. 4 shows a cross-sectional end elevation through a stem 2 and in which the projections 7 are located at the corners 15 of the stem. Thus, the projections now assume an L or crescent shape in cross-section. Once again the projections can be teardrop shaped and they can be mounted with their narrow ends pointing towards the proximal or distal ends of the stem. Again, they can be secured by any of the means described in FIGS. 1, 2 or 3.

Although described with regard to a stem of rectangular cross-section the function of this construction is to provide the projections on the corners of the stem so that the stem could be triangular, square or rectangular or any other convenient shape.

In the arrangements described above the stems tend to have at least two flat sides but it will be appreciated that the invention can also be applied to stems of any cross-section, even if they are curved, for example oval or circular.

In certain constructions the proximal portion of the stem may not be central in the canal into which it is to be inserted and the shape of the projections 7 can therefore be of different dimensions around the stem to ensure that it is guided as desired.

What is claimed is:

1. A prosthesis provided with a stem for fixation with cement in a bone socket, the proximal portion of the stem being provided with a number of shaped projections which are dimensioned to contact the inner wall of the bone socket and to act to guide the proximal end of the stem therein wherein said projections are attached to said stem by a releasable adhesive which releases upon the action of shear force acting thereon generated from the downward movement of the stem in the bone socket after initial implantation.

2. The prosthesis as claimed in claim 1 in which said projections are of teardrop shape facing towards the proximal or distal ends of the stem.

3. The prosthesis as claimed in claim 1 in which said release of said releasable adhesive under the action of said shear forces is enhanced by providing a smooth surface on the projection and a smooth surface on the stem.

4. The prosthesis as claimed in claim 1 in which the projections are made from a synthetic material.

5. The prosthesis as claimed in claim 4 in which the projections are made from polymethylmethacrylate (PMMA).

6. The prosthesis as claimed in claim 1 in which said stem has a polygonal cross-sectional shape with said projections located on corners of the stem.

7. The prosthesis as claimed in claim 1 in which the shaped projections are of different shaped around the stem.

8. The prosthesis as claimed in claim 1 in which said projections are carried on a band which is located on the proximal portion of the stem.

9. The prosthesis as claimed in claim 11 in which the band is made from metal or a synthetic material.

10. A prosthesis provided with a stem for fixation with cement in a bone socket, the proximal portion of the stem being provided with a number of shaped projections which are dimensioned to contact the inner wall of the bone socket and to act to guide the proximal end of the stem therein wherein said projections are attached to said stem by a sheer pin extending into a hole in the stem which pin releases upon the action of shear force, acting thereon generated from the downward movement of the stem in the bone socket after initial implantation by shear pins.

11. The prosthesis as set forth in claim 10 wherein the stem is designed to allow its downward movement after implantation.

12. The prosthesis as set forth in claim 11 wherein the stem is highly polished.

13. The prosthesis as claimed in claim 10 in which said projections are of teardrop shape facing towards the proximal or distal ends of the stem.

14. The prosthesis as claimed in claim 10 in which the projections are made from a synthetic material.

15. The prosthesis as claimed in claim 13 in which the projections are made from polymethylmethacrylate.

16. The prosthesis as claimed in claim 10 in which said stem has a polygonal cross-sectional shape with said projections located on corners of the stem.

17. The prosthesis as claimed in claim 10 in which the shaped projections are of different shapes around the stem.

18. The prosthesis as claimed in claim 10 in which said projections are carried on a band which is located in the proximal portion of the stem.

19. The prosthesis as claimed in claim 10 in which the band is made from metal or a synthetic material.

20. The prosthesis as set forth in claim 1 wherein the stem is designed to allow its downward movement after implantation.

21. The prosthesis as set forth in claim 20 wherein the stem is highly polished.

* * * * *

UNITED STATES PATENT AND TRADEMARK OFFICE
CERTIFICATE OF CORRECTION

PATENT NO.   : 6,123,730
DATED        : September 26, 2000
INVENTOR(S)  : Ling et al.

It is certified that error appears in the above-identified patent and that said Letters Patent is hereby corrected as shown below:

Column 1, line 9, after "of" insert -- the --.
Column 1, before line 17, insert -- SUMMARY OF THE INVENTION --
Column 3, line 14, after "force" insert -- , --.
Column 3, line 32, "shaped" should read -- shapes --.
Column 4, line 36, "11" should read -- 8 --.

Signed and Sealed this

Fifteenth Day of May, 2001

Attest:

NICHOLAS P. GODICI

*Attesting Officer*     *Acting Director of the United States Patent and Trademark Office*